United States Patent
Mershin et al.

(10) Patent No.: US 11,997,956 B2
(45) Date of Patent: Jun. 4, 2024

(54) METHOD FOR MYCOTECTURE

(71) Applicants: Massachusetts Institute of Technology, Cambridge, MA (US); Standard Bank Group Limited, Johannesburg (ZA)

(72) Inventors: Andreas Mershin, Arlington, MA (US); Christopher Maurer, Cleveland Heights, OH (US); Patritsia Maria Stathatou, Boston, MA (US); Carolyn Margaret Cameron-Kirksmith, Johannesburg (ZA)

(73) Assignees: Massachusetts Institute of Technology, Cambridge, MA (US); Standard Bank Group Limited, Johannesburg (ZA)

(*) Notice: Subject to any disclaimer, the term of this patent is extended or adjusted under 35 U.S.C. 154(b) by 71 days.

(21) Appl. No.: 17/648,105

(22) Filed: Jan. 14, 2022

(65) Prior Publication Data

US 2022/0217923 A1 Jul. 14, 2022

Related U.S. Application Data

(60) Provisional application No. 63/137,608, filed on Jan. 14, 2021.

(51) Int. Cl.
*A01G 18/20* (2018.01)
*A01G 18/00* (2018.01)
(Continued)

(52) U.S. Cl.
CPC ............. *A01G 18/00* (2018.02); *A01G 18/20* (2018.02); *A01G 18/50* (2018.02); *A01G 18/70* (2018.02); *C12N 1/14* (2013.01)

(58) Field of Classification Search
CPC . A01G 2/00; A01G 7/00; A01G 18/10; A01G 18/20; A01G 18/50; A01G 18/70
(Continued)

(56) References Cited

U.S. PATENT DOCUMENTS 4,443,969 A * 4/1984 Hanacek ................ A01G 18/00
47/1.1
8,227,224 B2 7/2012 Kalisz et al.
(Continued)

FOREIGN PATENT DOCUMENTS

CA 2915179 A1 6/2017
CN 104350940 A 2/2015
(Continued)

OTHER PUBLICATIONS

Yahia, E. M., Gutiérrez-Orozco, F., & Moreno-Pérez, M. A. (2017). Identification of phenolic compounds by liquid chromatography-mass spectrometry in seventeen species of wild mushrooms in central Mexico and determination of their antioxidant activity and bioactive compounds. Food Chemistry, 226, 14-22. https://doi.org/10.1016/j.foodchem.2017.01.044.
(Continued)

*Primary Examiner* — David J Parsley
(74) *Attorney, Agent, or Firm* — Dunlap Bennett & Ludwig, PLLC

(57) ABSTRACT

A method of making a food source or medicinal composition and a mycotecture construction unit includes (a) cultivating a mycelium/substrate composite and edible mushrooms, and (b) manufacturing the mycotecture construction unit. A mycelium inoculum is formed of a preselected fungus and used to inoculate a substrate. Mycelium are grown in the inoculated substrate in a growing column and edible mushrooms are harvested from the mycelium, leaving a mycelium-substrate composite. The manufacture of the mycotec-
(Continued)

ture construction unit includes placing the mycelium-substrate composite into a modular, reconfigurable press having a cavity with a predetermined shape; pressing the mycelium-substrate composite at a predetermined pressure; and heating the mycelium-substrate composite in a heating chamber. The construction unit is packaging, an insulation panel, a building construction material, or a household fitting with excellent compression strength, compressive modulus, flexural strength, flexural modulus, insulative properties, and fire retardant properties.

14 Claims, 10 Drawing Sheets

(51) Int. Cl.
*A01G 18/50* (2018.01)
*A01G 18/70* (2018.01)
*C12N 1/14* (2006.01)

(58) Field of Classification Search
USPC .................................. 47/1.01 R, 1.01 F, 1.1
See application file for complete search history.

(56) References Cited

U.S. PATENT DOCUMENTS

| | | | |
|---|---|---|---|
| 8,298,809 B2 | 10/2012 | Kalisz et al. | |
| 8,298,810 B2* | 10/2012 | Rocco | B01F 25/211 |
| | | | 435/174 |
| 8,313,939 B2* | 11/2012 | Kalisz | B01F 25/211 |
| | | | 435/174 |
| 9,485,917 B2 | 11/2016 | Bayer et al. | |
| 10,144,149 B2 | 12/2018 | McIntyre et al. | |
| 11,343,979 B2* | 5/2022 | Mueller | A01G 18/22 |
| 11,359,074 B2* | 6/2022 | Kaplan-Bie | C08K 3/16 |
| 11,420,366 B2* | 8/2022 | McIntyre | B29C 44/3415 |
| 2014/0069004 A1* | 3/2014 | Bayer | A01G 18/64 |
| | | | 47/58.1 R |
| 2014/0173977 A1* | 6/2014 | Juscius | A01G 18/20 |
| | | | 47/1.1 |
| 2015/0101509 A1 | 4/2015 | McIntyre et al. | |

FOREIGN PATENT DOCUMENTS

| | | | |
|---|---|---|---|
| CN | 105503289 A | | 4/2016 |
| CN | 212507024 U | | 2/2021 |
| EP | 3828260 A1 | | 6/2021 |
| ES | 2435458 | * | 12/2013 |
| ES | 2497415 A1 | | 9/2014 |
| JP | 2004-166583 | * | 6/2004 |
| WO | 2014195641 A1 | | 12/2014 |
| WO | 2020136447 A1 | | 7/2020 |

OTHER PUBLICATIONS

BIOFAB: Mycelium packaging: Auckland. Bio Fab—NZ. (Dec. 2, 2021). Retrieved Dec. 17, 2021, from https://www.biofab.bio/.
Ecovative. (n.d.). Retrieved Dec. 2, 2021, from https://ecovative.com/.
Sande, D., Oliveira, G. P., Moura, M. A., Martins, B. de, Lima, M. T., & Takahashi, J. A. (2019). Edible mushrooms as a ubiquitous source of essential fatty acids. Food Research International, 125, 108524. https://doi.org/10.1016/j.foodres.2019.108524.
Elsacker, E., Vandelook, S., Brancart, J., Peeters, E., De Laet, L. (2019). Mechanical, physical and chemical characterisation of mycelium-based composites with different types of lignocellulosic substrates. PLOS One, 14(7). https://doi.org/10.1371/journal.pone.0213954; Editor: Deniz Aydemir, Bartin University, Turkey Received: Feb. 23, 2019 Accepted: Jul. 1, 2019.
Marijana Popović, Antonela Matana, Vesela Torlak, Dubravka Brdar, Ivana Gunjača, Vesna Boraska Perica, Maja Barbalić, Ivana Kolčić, Ante Punda, Ozren Polašek, Caroline Hayward & Tatijana Zemunik (2019) The effect of multiple nutrients on plasma parathyroid hormone level in healthy individuals, International Journal of Food Sciences and Nutrition, 70:5, 638-644, DOI: 10.1080/09637486.2018.1551335.

* cited by examiner

METHOD FOR MYCOTECTURE

CROSS-REFERENCE TO RELATED APPLICATION

This application claims the benefit of priority of U.S. provisional application No. 63/137,608, filed Jan. 14, 2021, the contents of which are herein incorporated by reference.

BACKGROUND OF THE INVENTION

The present invention relates to agriculturally produced building materials and, more particularly, to methods and an apparatus for mycotecture as well as myco-foods (edible mushroom-based products) and myco-medicine (medicinal-mushroom based preparations) production. The application may also be referred to herein as Methods and Apparatus for Mycotecture, Mycofood, and Mycomaterials Production. The methods are tripartite in nature and are tunable.

Mushrooms grow quickly on agricultural waste (agri-waste) without sunlight or extensive irrigation, making nutritious, high-protein foods. Mycelium, the vegetative form of fungi, having rootlike branching hyphae that devour organic matter, is the organism that produces mushrooms in a stage called "fruiting". Mycelium secrete enzymes that dissolve their food and bond with the substrate at a cellular level. Some species of mycelium have also been shown to be useful for bioremediation of oil spills, toxic chemicals, and acidic radioactive waste, and for quickly breaking down plastics such as polyester polyurethane.

International markets exist, and global demand is growing, for mushroom-based foods (mycofoods) and medicines across an increasing variety of species. Mycofoods may be used to address the ever-increasing problem of malnutrition in Sub-Saharan Africa and beyond. Malnutrition-related diseases increase entirely preventable healthcare costs that span the entire lifetime of those malnutritioned at youth, causing socio-economic losses and needlessly lower the region's gross domestic product. The problem of malnutrition is exacerbated by homelessness.

Mycofoods are nutritional powerhouses already shown capable of being grown on limited square footage using up to two orders of magnitude less water, energy, and time than beef or corn of similar nutritional value (by weight post-dehydration). Mushrooms have a nutritional value that some consider qualifies mushrooms as (super)foods. For example, an oyster mushroom uses 3 L water to produce a gram of protein. A serving of oyster mushroom provides 0.4 g fat, 6.5 g carbohydrates, 2.3 g fiber, and 3.3 g protein for 43 calories. In contrast, ground beef uses 52 L water to produce a gram of protein. A serving of ground beef provides 17.4 g fat, no carbohydrates or fiber, and 27 g protein for 272 calories. Chickpeas and rice require even more water to produce a gram of protein, at 114 L and 79 L of water per gram of protein, respectively. The prior art is replete with research on the nutritional value of mushrooms. Popović, et al. ("The effect of multiple nutrients on plasma parathyroid hormone level in healthy individuals", International Journal of Food Sciences and Nutrition, 2019, Vol. 70, No. 5, pp. 638-644) included mushrooms in a study of Plasma parathyroid (PTH) levels in healthy adults and found that there is a positive relationship between diets with mushrooms and plasma PTH levels. Yahia, et al. ("Identification of phenolic compounds by liquid chromatography-mass spectrometry in seventeen species of wild mushrooms in Central Mexico and determination of their antioxidant activity and bioactive compounds", Food Chemistry, 1 Jul. 2017, Vol. 226, pp. 14-22) breaks down 17 different species of wild mushrooms in search of phenolic compounds to assess their antioxidant properties. Sande, et al. ("Edible mushrooms as a ubiquitous source of essential fatty acids", Food Research International, 2019, 125, 108524) reports on the use of mushrooms as a source of essential fatty acids.

Mushrooms have also been known for other uses, such as the use of ember fungus to transport fire. Mushrooms may also be used as a source of enzymes, for example to remove stains, and may be a source of components for cosmetics, as well as medicinal preparations, particularly prevalent in the practices of many traditions in Eastern medicine as well as modern nutrition-based wellness protocols.

Concurrently, "mycotecture", a fast-emerging suite of processes, produces inexpensive, high-performance materials for housing, packaging, and insulation, with edible mushrooms being a natural byproduct of these processes. Self-sustaining shelter construction and food-production infrastructure is of general interest to all geographic regions. Ecovative and a handful of similar US, European, and New Zealand companies involved in mycotecture are solely focused on materials production and scaling up mushroom growth that is not ideal for food production. For example, a New Zealand startup is focused on producing mycotecture packaging material replacements for Styrofoam without food production. Even so, ice boxes and coolers are currently largely made of plastic-based material which is not environmentally friendly and is difficult to dispose of at the end of its useful life.

As can be seen, there is a need for inexpensive, easy to produce building materials from food production byproducts.

SUMMARY OF THE INVENTION

Applicant has shown the feasibility of scalable food production with low technology and skill, with zero chemical pesticides and herbicides, at a fraction of the time and labor costs of conventional food growing practices, while also producing structurally sound materials for insulation, packaging, and architecture (known as mycotecture).

In one aspect of the present invention, a method of making a food source and a mycotecture construction unit is provided, comprising: (a) cultivating a mycelium/substrate composite and edible mushrooms, including forming a mycelium inoculum of a preselected fungus; inoculating a substrate with the mycelium inoculum; growing mycelium in the substrate from the mycelium inoculum; and harvesting the edible mushrooms from the mycelium, leaving a mycelium-substrate composite; (b) and manufacturing the mycotecture construction unit, including; placing the mycelium-substrate composite into a press having a cavity with a predetermined shape; pressing the mycelium-substrate composite at a predetermined pressure; and heating the mycelium-substrate composite.

In another aspect of the present invention, a modular mycotecture production system is provided, comprising: a growing column; a pasteurization apparatus; a colonization chamber; a fruiting chamber; a modular, reconfigurable press; a heating chamber; and a drying room.

These and other features, aspects and advantages of the present invention will become better understood with reference to the following drawings, description, and claims.

DETAILED DESCRIPTION OF THE INVENTION

Figure 1:
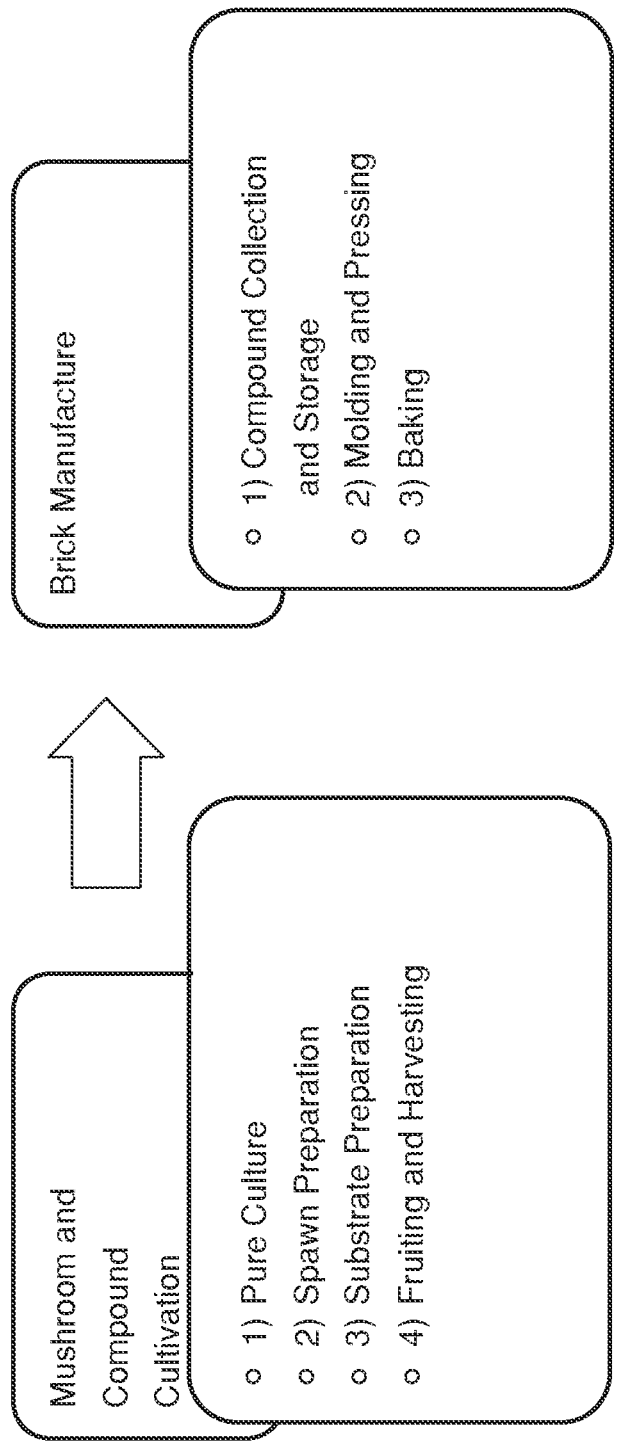
FIG. 1 is a flow diagram of a mycofood and mycotecture production method according to an embodiment of the present invention.
Figure 2A:
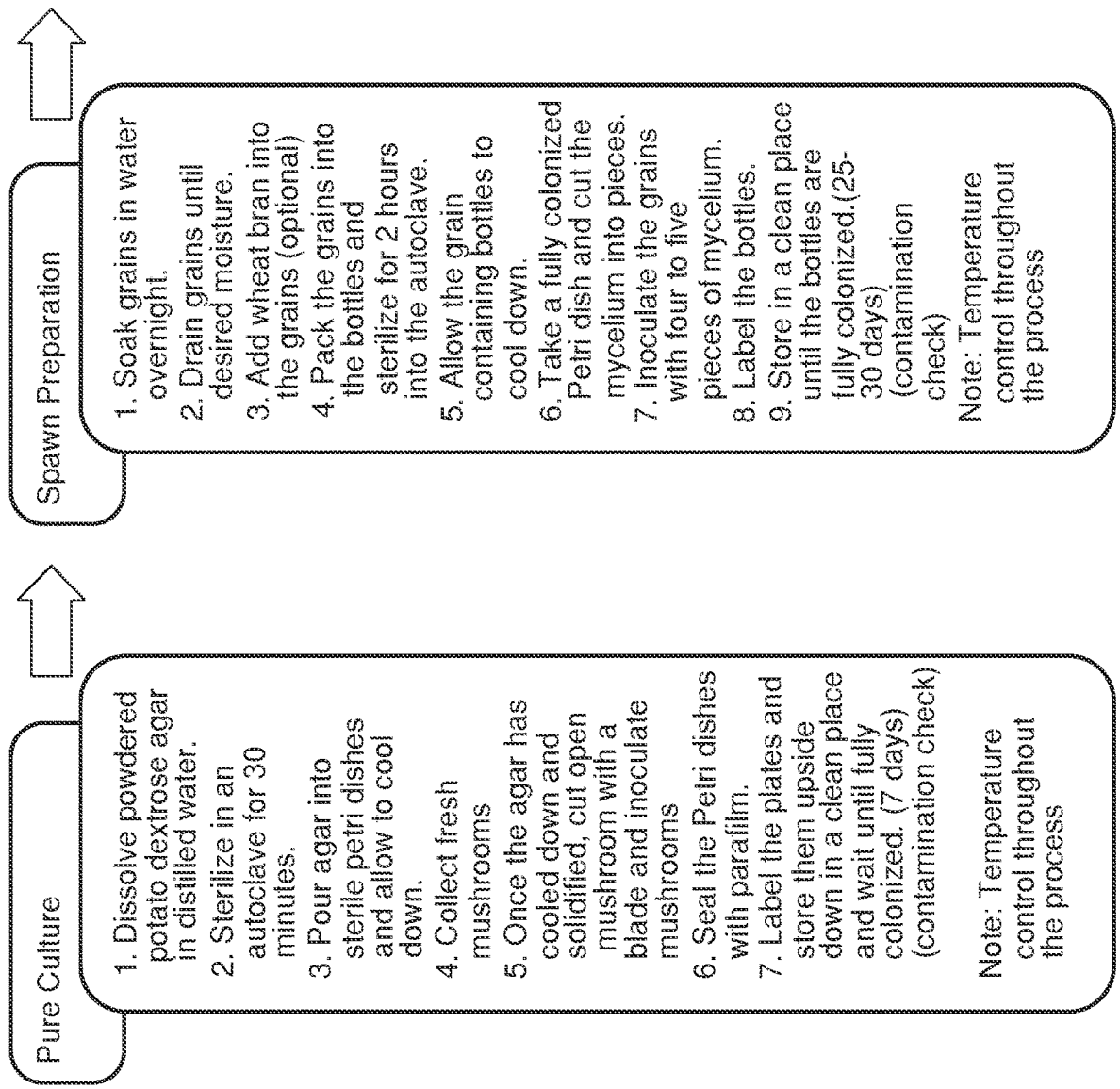
FIG. 2A is a flow diagram of a culture preparation step and a spawn preparation step thereof.
Figure 2B:
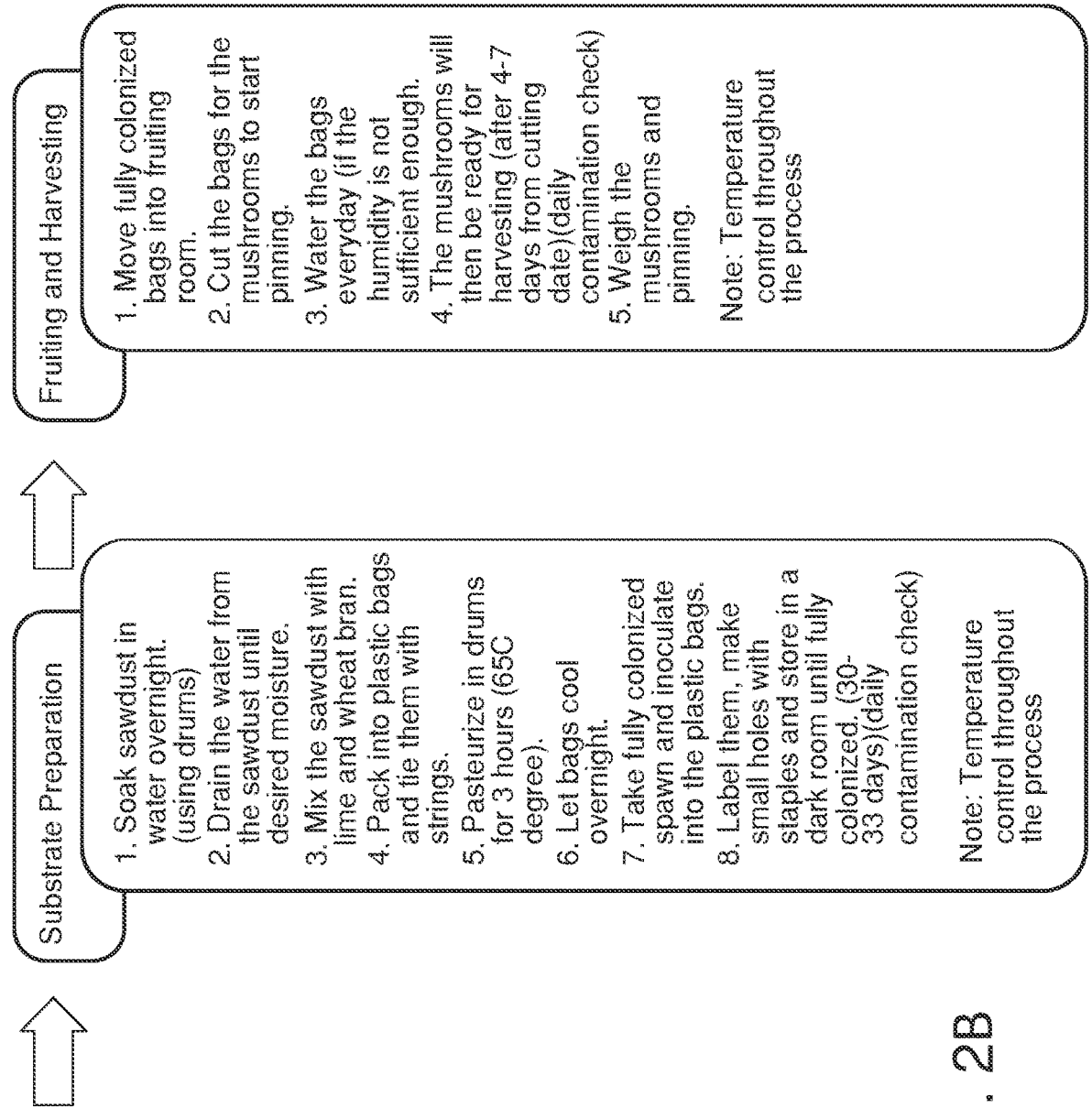
FIG. 2B is a flow diagram of a substrate preparation step and a mushroom cultivation step thereof.
Figure 3:
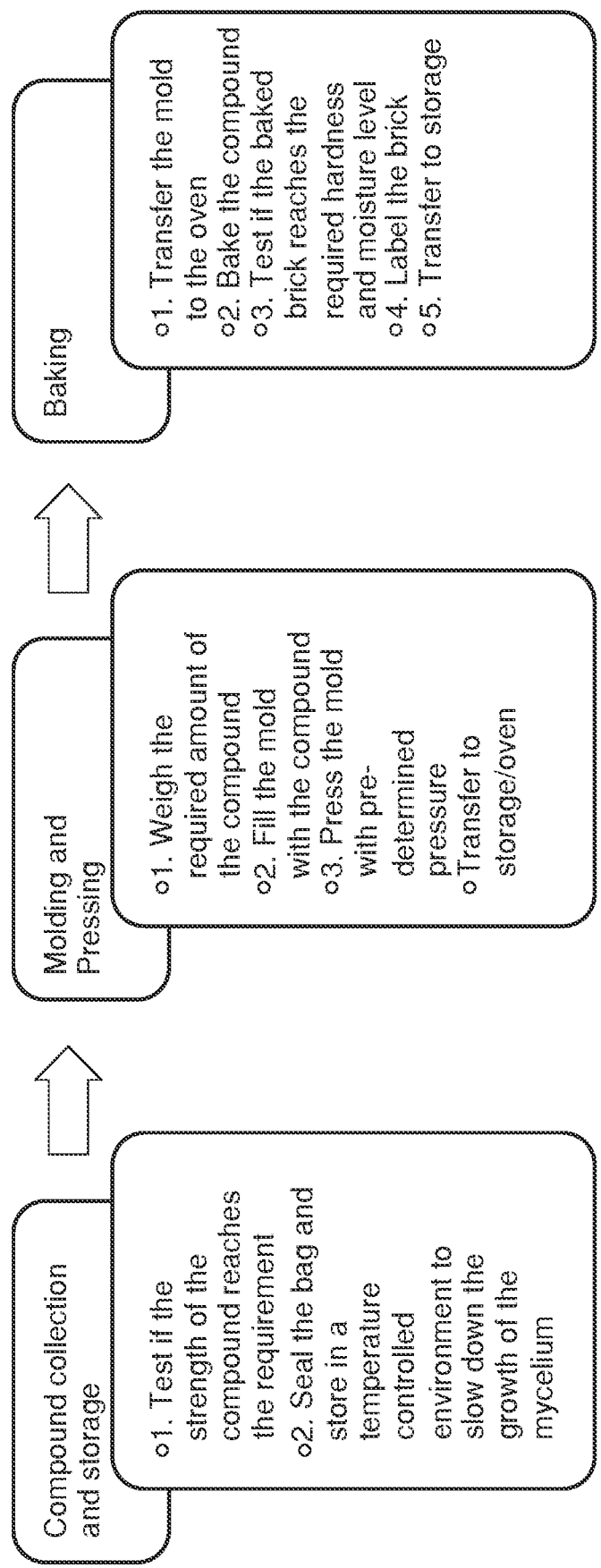
FIG. 3 is a flow diagram of brick manufacture steps thereof.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

As used herein, the term "mycotecture" refers to building, packaging, and insulative materials, as well as potentially dual-purpose materials including edible or medicinal materials, comprising cultivated mycelium, including construction materials for housing, packaging, and insulation, and architectural structures constructed therefrom. The mycotecture methods and apparatus described herein are sometimes referred to as BioHab or BioFab self-sustaining self-reproducing housing or as MycoHab (the prefix myco- is intended to indicate the common origin in fungi for the variety of end products).

Formwork refers to forming the inoculated matter into a strong, light shape, under pressure for a predetermined time.

As used herein, the term "fully colonized" refers to a condition of a substrate in which it has been completely consolidated and encompassed by the mycelium.

The term "lime" as used herein refers to a composition containing calcium oxide or calcium hydroxide.

Broadly, one embodiment of the present invention is a modular, generalizable mycotecture protocol platform applied in conjunction with a novel substrate treatment, growth, harvest, packaging and monitoring and quality control methodology including a modular, reconfigurable press and heat operation to allow form and shape customization and iterative optimization of material properties.

Applicants have discovered that mycelium may be used to grow mushrooms as food and subsequently used to produce building materials for shelter, i.e., the waste from the mushroom cultivation may be used to create building materials. Both products may be used as a source of income. The mycelium-based construction materials are carbon negative and do not overly pollute the environment. This bonded substrate may be formed to any shape with time, pressure, and heat to create a light building material that is stronger than concrete.

Any suitable mushroom-producing mycelium may be used. The species that may be cultivated in the inventive method are not limited. For example, oyster mushrooms, shiitake mushrooms, and *Ganoderma* (*Reishi*) may be cultivated. In some cases, black fungus may be cultivated. Depending upon the substrate used, button mushrooms and portabella mushrooms may be cultivated in some embodiments. Mycofoods produced by the inventive method have shown up to two orders of magnitude improvement on pound-for-protein-pound comparison to beef on every metric: less than 1/1000th of the land, less than 1/100th of the water, time and energy required for meat of equivalent nutritional and retail market value.

A sturdy, re-usable, inflatable scaffolding or form may be used to guide placement of mycelium bricks produced according to an embodiment of the present invention for construction of housing. In some embodiments, an inflatable device may be configured to compress mycelium/substrate composite into packaging, insulation panels, and household fittings that were previously made of plaster, foam, or fiberglass.

Deployment of the inventive, tri-partite method marks a field-transforming event: for the first time, a food-producing process that also creates structural and insulative building materials (mycotecture) may be supported in an integrated workflow with modular composition while enabling the generation of land-use and carbon-offset credits by tracking the actions conducted in the production process securely online. This method allows for the first in situ production of different products controlled by the results of basic if/then logic operations responsive to global and local physicochemical conditions, from molecular species-specific concentrations to pH, temperature, light, applied heat, and applied pressure, to control the structural and other physicochemical parameters of the final product. A range of useful products may be made, including edible and/or medicinal mushrooms, green packaging and insulation, and structurally sound, aesthetically appealing and safety-rated building materials. The compressed mycelium/substrate composite of the present invention exhibits a density that makes the bricks light and buoyant. The bricks also attenuate sound. The materials may also exhibit thermal resistance and provide fire protection. The bricks may act as a Class 1 firewall, similar to gypsum board. In some cases, the bricks may exhibit a thermal conductivity, such as about 0.06 W/mk, that outperforms rigid expanded polystyrene (EPS). The ultimate impact may be a dramatic expansion of the number and efficacy of mycotecture products available for the construction and other industries, such as medicines and therapies, as well as a variety of food products.

This invention is of particular interest to the carbon negative, agricultural, human and animal food production, and construction/packaging/insulation materials industries, gourmet food and medicinal supplement industries, and chemical, flavorant, food additive, odorant, fragrance, cosmetic and biomanufacturing industries (including experimental protocols and biomedicines, biofuels, chemicals, dietary supplements, etc.).

The process comprises two main components: cultivation of a mycelium/substrate composite and edible mushrooms under temperature-controlled conditions and manufacture of bricks or other mycomaterials by molding, pressing, and baking the composite. The mycelium composite is an environmentally friendly material because it can be treated without using polluting substances. At the end of its life, the material is completely biodegradable and compostable.

Cultivating and harvesting the fruiting mushrooms according to the inventive process does not require sunlight or irrigation, as the mushrooms absorb humidity, carbon, and oxygen from the surrounding air and obtain nutrients and nitrogen from the growth substrate. For about the first 3 weeks, the mycelium may grow in ambient atmospheric humidity, obtaining moisture from the hydrated substrate. Edible mushrooms grow with an atmospheric humidity of about 80% or more, such as about 85% to about 95% RH to prevent mushroom dehydration, without the addition of water. This growth cycle may be accelerated by use of highly efficient, inexpensive humidifiers. Even so, mushrooms still require less than 1% of the water added by irrigation that is necessary to grow any food of comparable protein and nutrient content. This process produces the composite material for the bricks. Mycelium composite is an environmentally friendly material because it can be treated without using polluting substances. At the end of its life, the material is completely biodegradable and compostable.

The mycelium substrate is not particularly limited and may vary with the species of mycelium cultivated. The combinations of mycelium and biomass substrate may be optimized to achieve selected results. The composite material resulting from mushroom farming is influenced by the substrate (food) that the mushrooms grow on. The substrate *Acacia mellifera*, i.e., the blackthorn "encroacher bush", for example, produces a mycelium-substrate composite with high compressive strength. By harvesting the bush, grasslands may regrow that can feed cattle and antelope. The biomass from the bush is an excellent substrate for growing gourmet mushrooms. Other substrates may include, but are not limited to, sawdust from industrial waste; straw from agricultural waste; Giant Kelp (*Macrocystis pyrifera*); Fish Scales; Cacti or succulent plants; bamboo; building waste; and industrial hemp (*Cannabis sativa* plant species). Giant Kelp is the largest algae in the world and the fastest growing organism on earth. As it contains many compounds such as iodine, potassium, other minerals vitamins and carbohydrates, giant kelp been used as a dietary supplement. Some of the world's largest giant kelp forests are found off the coast of South Africa and Namibia. Additional substrates may in some cases include brewery waste, cacao shells, coconut fiber, straws, textiles, garden waste, hair, leaves, manure, nut casings, seed hulls, rice, oils, paper products, and by-products of corn, cotton, coffee beans, soybeans, rice, straw, sugarcane, and tobacco.

Cultivation may begin with preparing a pure culture, spawn, and substrate. The culture may be prepared by preparing sterile petri dishes containing sterilized agar (e.g., powdered potato dextrose agar dissolved in distilled water), collecting fresh mushrooms, and inoculating spores from the mushroom onto the agar. The dishes may be sealed with PARAFILM™, a semi-transparent, flexible film composed of a blend of waxes and polyolefins; labeled; and stored for about 7 days or until fully colonized. The spawn may be commercially sourced or may be produced by inoculating prepared grain with mycelium collected from the fully colonized petri dishes. The grain may be prepared by soaking it in water overnight, draining the water, in some cases, adding wheat bran, packing the grain and wheat bran into bottles, sterilizing the bottles by autoclave for about 2 hours or more, and cooling the bottles. The bottles may be labeled and stored for about 25-30 days or until fully colonized. The spawn may be stored in a cold environment and preferably used within a matter of weeks.

The substrate e.g., *A. mellifera* sawdust, may be prepared by soaking it in water overnight and draining the water. The soaked substrate may be brought to about a 60% moisture content by setting it in the sun to dry until the substrate clumps but does not release moisture when squeezed. About 10% by weight bran may be added to the sawdust.

In some embodiments, the substrate may be pasteurized by packing it into plastic bags that are tied closed and heated (e.g., in 800 liter drums covered with a polypropylene top) for at least about 3 hours at a temperature of at least about 65° C., such as for about 24 hours at a temperature of about 100° C. using steam at atmospheric pressure. The pasteurized substrate bags may be cooled to below about 26° C. and inoculated, preferably in front of a laminar flow hood in a clean room, with spawn from the fully colonized bottles at an amount of about 10% of the total mass, and fastened, e.g., with a tie.

In some embodiments, the soaked and partially dried sawdust may be pasteurized by loading it into a ribbon blender with about 10% bran. The material may be heated with a steam boiler to about 65° C. and spun for about an hour, checking the temperature periodically. After cooling to below about 26° C., the heated material may be inoculated with grain spawn at an amount of about 10% of the total mass and mixed in the blender for about 10 minutes. The bottom gate of the ribbon blender may be emptied into reusable hanging bags, the top of the bags may be fastened.

In some embodiments, the ribbon blender may be powered by solar photovoltaic cells.

The inoculated bags may be labeled and stored in a colonization chamber or dark room at about 18° C. for about 30-33 days or until fully colonized. The bags may then be moved into a fruiting chamber or fruiting room maintained at about 18° C. to about 23° C. The bags may be cut to enable mushrooms to pin. The bags may be watered every day or the chamber may be humidified to maintain a relative humidity of about 80% or more in the fruiting chamber, such as about 85-95% RH. After about 4-7 days, mushrooms may be harvested, weighed, and packaged. Contaminated bags may be removed.

In some embodiments, the cultivation may be performed using a vertical transparent grow column or form, which may be made of an acrylic polymer such as PLEXIGLAS®. For example, the grow column may have an upper panel with grommets through which rope may be run to suspend the bags. The upper panel may also have an inner solid foam panel with a smaller width and length than the upper panel. A lower panel may be fastened to the opposite end of the column. The grow forms may be installed within hoop houses or rammed earth structures, for example. The grow forms may be wiped down with at least about 70% by volume isopropyl alcohol.

During the cultivation process, the growing bags may be monitored for contamination and data may be recorded. Temperature and humidity are two of the most important factors influencing the quality and productivity of the final product. Other data points that may be collected include weight, hardness, pressure, and time, etc.

After mushrooms have been harvested, the cultivated mycelium-substrate composite may be used to manufacture bricks or other building products, such as furniture or household fittings. The post-harvest composite may be collected, stored, and sealed in a temperature-controlled environment to slow the growth of the mycelium and to maintain the strength. The composite may be further processed to make it suitable for pressing. The composite may be weighed to obtain a consistent amount of material, inserted into the molds, and pressed at a predetermined pressure into the shape of the bricks. In some embodiments, the pressed composite may be laminated.

The material in the bags may be moved to a press. The composite material may be pressed out of the bottom of the bag with a tamper. In some embodiments, a rolling conveyor may load composite material into the press from the bag. The press chamber may have any suitable dimensions, such as about 25 cm×about 25 cm×about 75 cm. A gate lever may be activated to lock the press. A press lever may activate a compression ram, which may hold the composite under pressure (e.g., 150 tons) for about 30 seconds. The gate lever may be activated to open the gate. An eject lever may be activated to eject the compressed block. The ram and eject levers may be reset.

The mold containing the compressed composite may be transferred to storage and/or to an oven to undergo a baking process to produce a brick having the hardness for construction purposes.

The compressed blocks may be moved to an oven or heating chamber, such as a modified shipping container with a LAMBORGHINI™ burner, and placed in a mold or form. In some embodiments, a plurality of steel forms may be provided with valved lines feeding steam to the forms in parallel. The forms may be heated by steam when a valve is turned to direct steam to the platens. Alternatively, heated oil may be used as the heat transfer medium. The heating chamber may be closed, and the molds heated for at least about 4 hours, such as about 12 hours at a temperature of about 180° C. with recirculating heat. The molds may be cooled overnight. Once the heated bricks have been removed from the form, they may be set in a drying room.

In some embodiments, a brick extraction tool is employed to remove the bricks from the molds.

The composite strength may be tested to ensure a predetermined strength is achieved. The compression strength may range, for example, from about 8 MPa to about 26 MPa or more. The surface hardness may be as high as about 39 MPa and the compressive modulus may be about 980 psi. Flexural strength of about 425 psi with a flexural modulus of about 275 MPa may be achieved. Impact strength is also excellent. Stress-strain graphs and flexural stress-strain graphs may be produced.

The hardness and moisture level may be tested to ensure they meet predetermined levels. The brick may be labeled and transferred to storage.

Tracing methods may be used to trace the final product back should there be any quality issue. Environmental impact via carbon sequestration, food safety, and provenance may be transparently validated by scientific methodologies via blockchain technology, enabling an organization to accumulate carbon sequestration credits. The data tracked, e.g., with a mobile device, may include one or more of the following: a quick response (QR) code, an Electronic Product Code (EPC), a Global Trade Item Number (GTIN), a Global Location Number (GLN), Purchase Order (PO), Lot/Batch Global Trade Item Number (LGTIN), Serialized Global Trade Item Number (SGTIN), Food Trust Product Identification (FTPI), FTPI plus lot number (LFTPI), FTPI plus serial number (SFTPI), Food Trust Location Identification (FTLI), FTLI plus sublocation (SFTLI), and Food Trust container Identification (FTLPN).

The mycelium-substrate composite is generally hygroscopic. In some embodiments, the mycelium-based building materials may be made waterproof. The outer surfaces may be covered by waterproofing material. In some embodiments, the composite bricks may be painted to render them waterproof. In other embodiments, a mud-lime rendering may be added in conjunction with a roof to protect the bricks from the elements. Many currently available waterproofing materials are not eco-friendly, not sustainable, and expensive. Preferably, the waterproofing material is eco-friendly, sustainable, and inexpensive.

In some embodiments, the mycelium/substrate composite may be formed into a non-toxic, biodegradable cooler or ice box having superior structural strength, insulative properties, and fire retardant properties. The Cooler/ice box may be an insulated "cabinet or chest" with a partition for ice or other substances to keep the contents frozen or cold. A mycelium composite-based cooler/ice box may be used for preserving or cooling food, beverages, etc. and to transport essential, lifesaving and desperately needed medicines and vaccines, especially across Africa.

Example

The following examples were performed on Applicant's joint experimental site at Brakwater outside Windhoek, the capital city of Namibia, at a grow-operation and construction material fabrication site established in part by the Buy-a-brick charitable foundation.

*Acacia mellifera*, also known as blackthorn or "encroacher bush", was mulched and used as substrate. *Acacia mellifera* is indigenous to Namibia and has been choking natural aquifers, grasslands, and cattle grazing lands.

May 11-15, 2020: Shipping containers serving as a "dark room" and a "fruiting room" were disinfected. Substrate was soaked for a day and drained the next day. The drained substrate was packed into growbags. The bags were cut to enable mushroom fruiting through the bags. The bagged substrate was pasteurized in drums. Seventy-seven bags were inoculated with fungal spawn under sterile conditions. The inoculated bags were placed on shelves in the dark room. The bags were transferred to the fruiting room for growth of mushrooms.

May 14-18, 2020: Substrate was soaked in drums, pasteurized, and inoculated.

May 18-22, 2020: Soaked substrate was drained and pasteurized. Bags of inoculated substrate in the "fruiting room" were watered. Some mushrooms were harvested. The dark room was divided into four sections. Three of the four sections were arranged for recording research in triplicate. Seventy-eight bags were inoculated. Three bags were pasteurized with 3% m/m peroxide. A humidifier was used to maintain humidity and an air conditioner was turned off to increase temperature. Materials included wheat bran, alcohol, and firewood.

May 25-Jun. 12, 2020: Substrate was soaked, drained, and pasteurized. Eleven bags of substrate were inoculated under sterile conditions. 4 kg of mushrooms were harvested and 1 kg packaged. 20+ bottles of spawn were produced by a bottle-to-bottle method. The colonization and fruiting room were both disinfected. Firewood was collected for pasteurization. Dried mushroom pins were removed from the bags and the fruiting room was watered. New fully colonized bags were relocated to the fruiting room. Some bags exhibited mold contamination and were isolated from the remaining bags in the fruiting room.

The mycelium composite resulting from mushroom farming using local Namibian encroacher bush (*Acacia mellifera*) as the substrate (food) resulted in a composite with inherent and impressive structural strength, and insulation, fire retardant/extinguishing, sound attenuating, and non-toxic properties.

Referring to FIGS. 1 through 10, FIGS. 1, 2A, 2B, and 3 are flow diagrams illustrating a mycofood and mycotecture production method according to an embodiment of the present invention as discussed in detail above.

Figure 4:
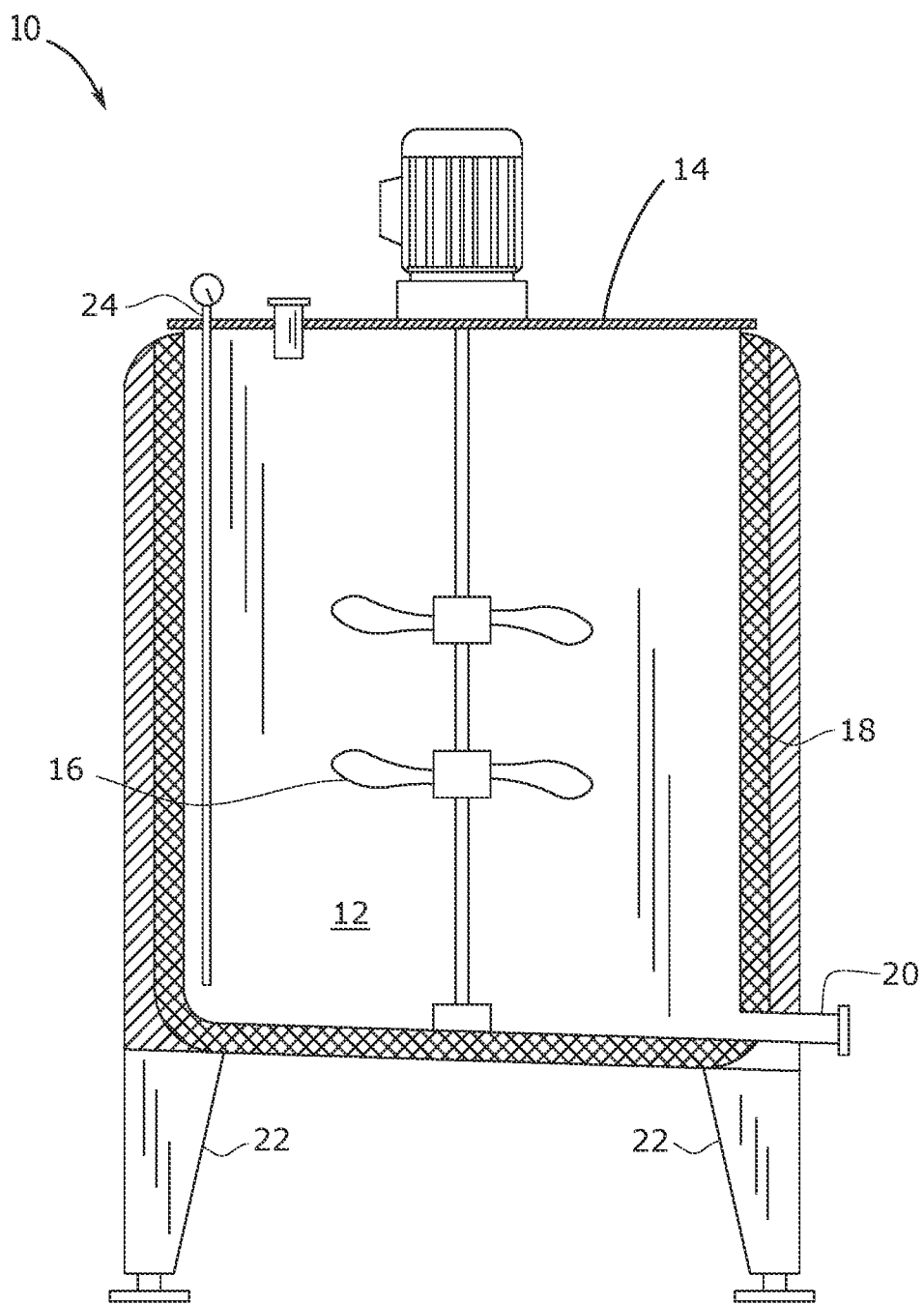
FIG. 4 is a sectional view of a substrate pasteurizer according to an embodiment of the present invention.

FIG. 4 illustrates a substrate pasteurizer 10 according to an embodiment of the present invention. The apparatus 10 comprises a vessel 12, in which the substrate may be heated, and a lid 14. As shown, the pasteurizer includes a central agitator 16, which may be used for substrate loaded loosely into the vessel 12. Alternatively, the pasteurizer 10 may lack an agitator to accommodate substrate loaded into the pasteurizer in containers, such as bags. As shown, the double wall 18 may circulate a heat transfer fluid such as steam around the substrate or steam may be introduced directly via inlet/outlet 20. The pasteurizer is shown elevated on legs 22, enabling introduction of heat from below the vessel. The temperature may be monitored by thermometer 24.

Figure 5:
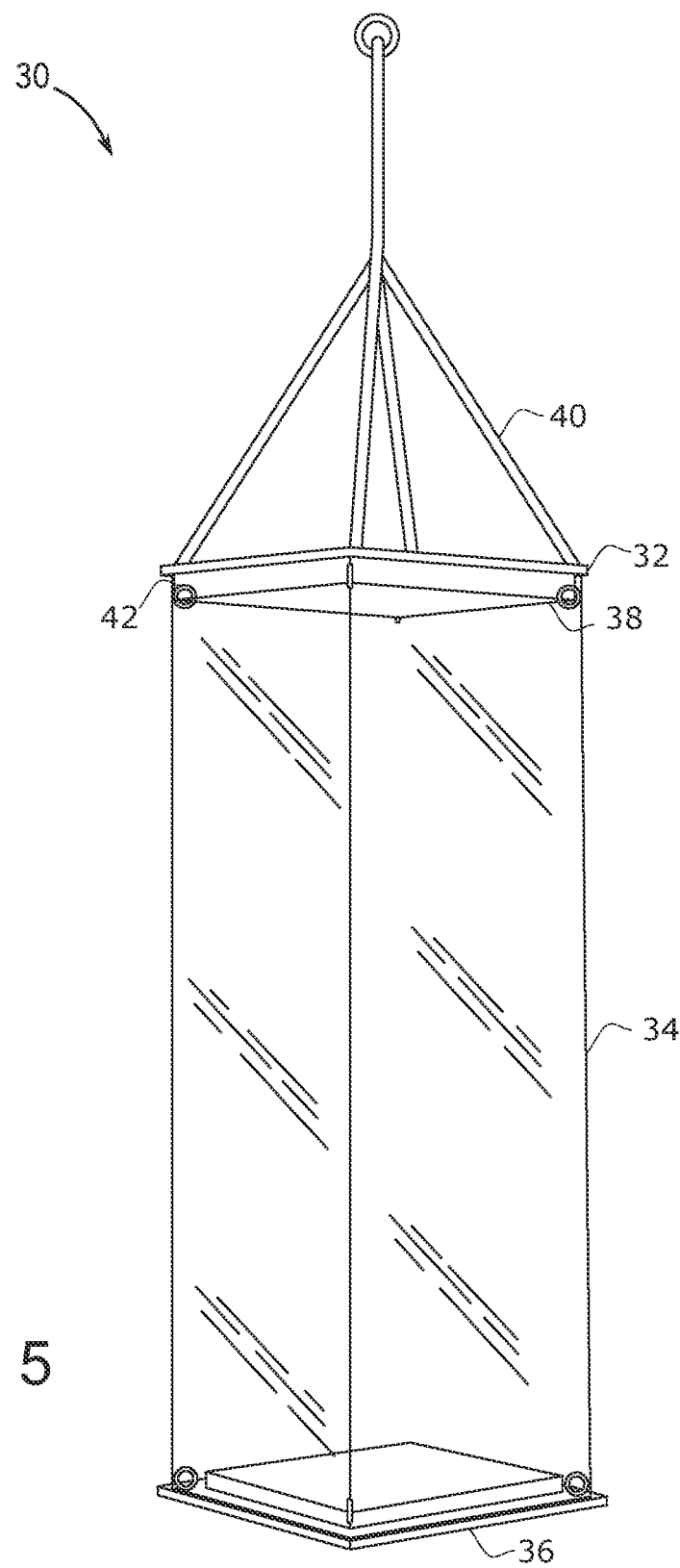
FIG. 5 is a perspective view of a growing column according to an embodiment of the present invention.

FIG. 5 illustrates a vertical growing column or form 30 for cultivation of mycelium. The column includes an upper panel 32, transparent sidewalls 34, and a lower panel 36. An inner solid foam panel 38 extends into the top of the column. The upper panel is suspended by rope 40 through grommets 42 in the upper panel.

Figure 6:
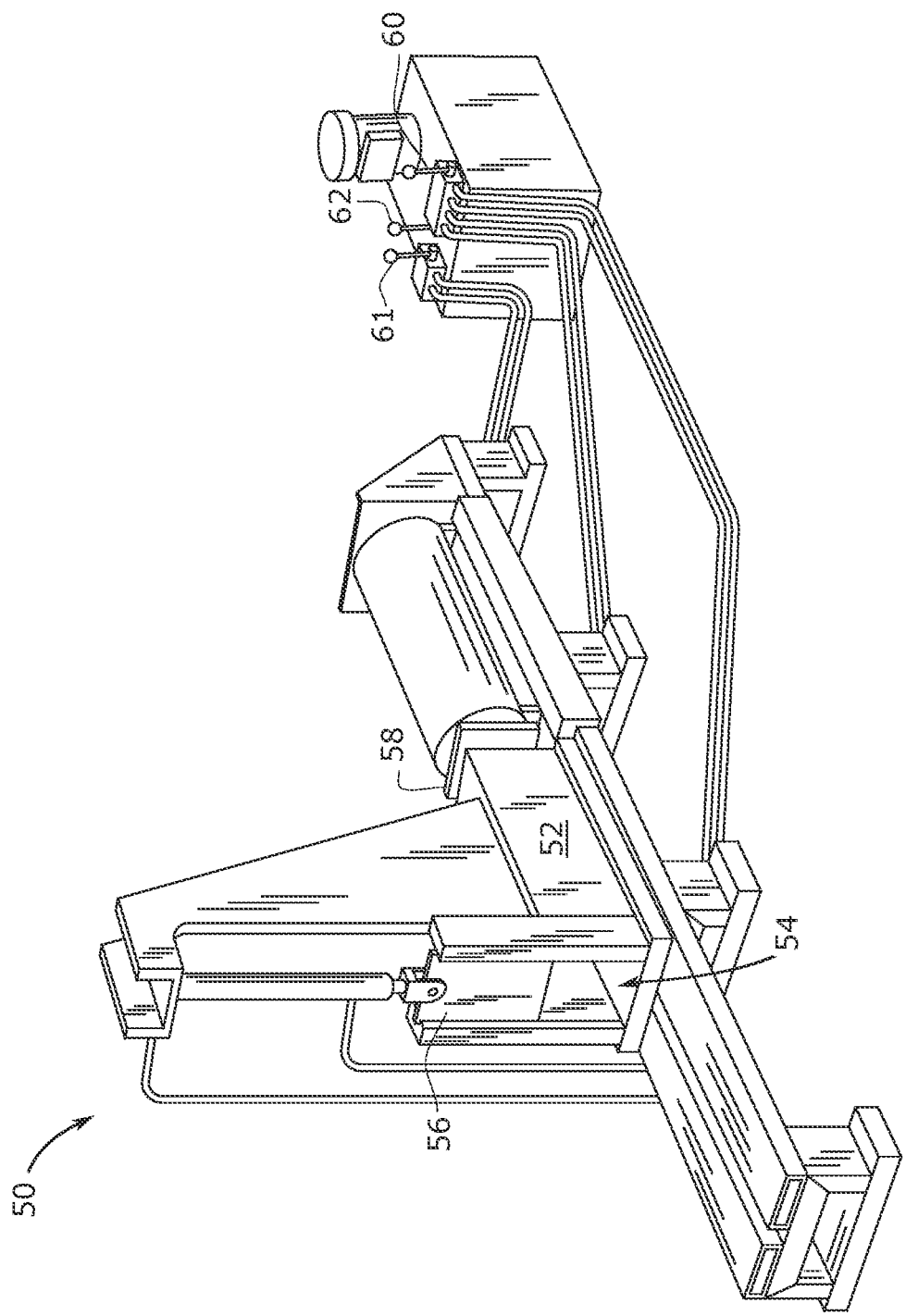
FIG. 6 is a perspective view of a mycelium/substrate composite press according to an embodiment of the present invention.

FIG. 6 illustrates a mycelium/substrate composite press 50 according to an embodiment of the present invention. The press 50 is modular, including a mold 52 having a cavity 54 into which the composite is loaded. A gate 56 is controlled by a first lever 60. A compression ram 58 is operated by a second lever 61. Once the composite has been compressed, the gate 56 may be opened and the resulting block is ejected, e.g., with the compression ram 58 using a third lever 62.

Figure 7:
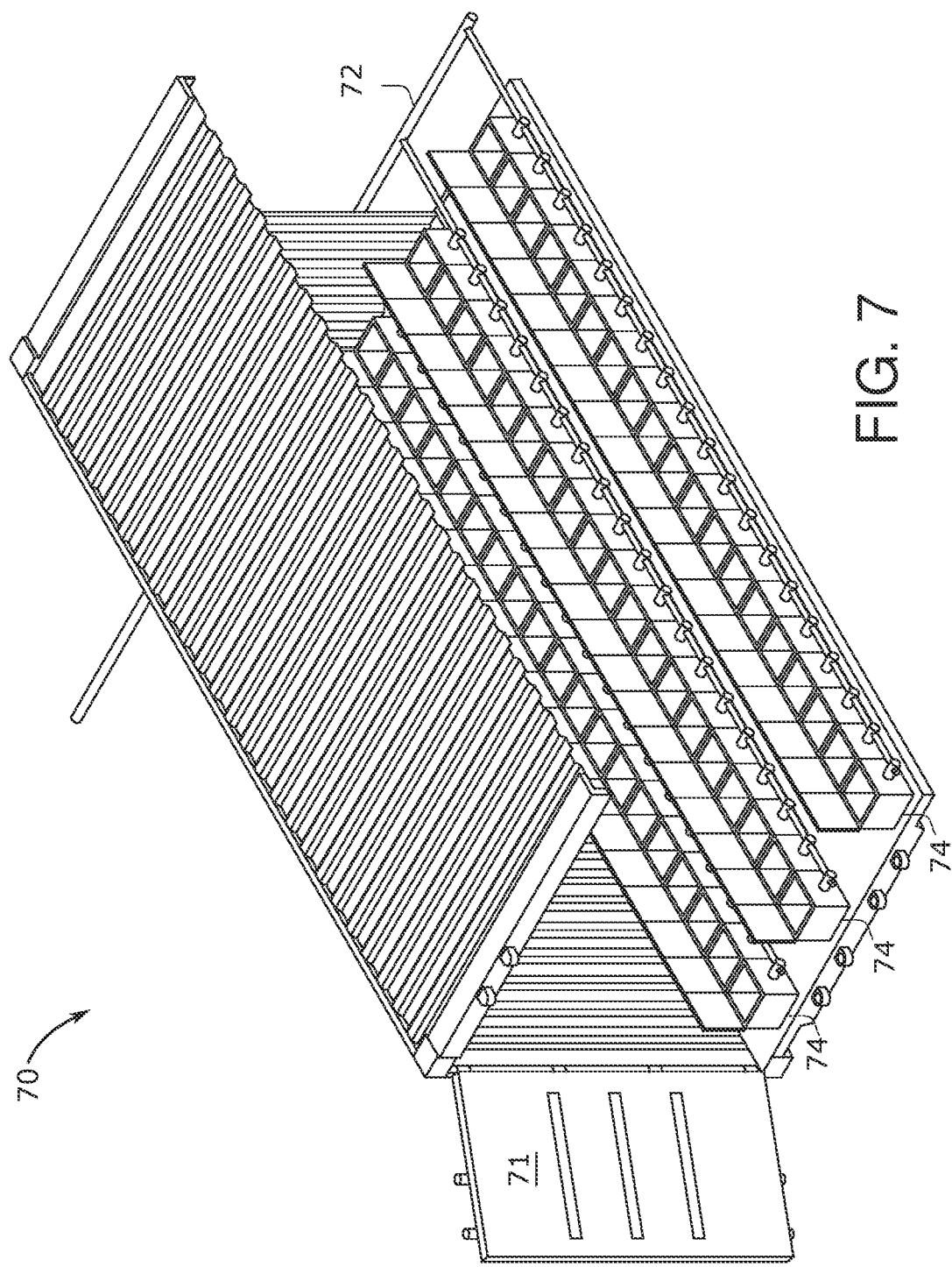
FIG. 7 is a partially cutaway perspective view of a heating chamber according to an embodiment of the present invention.

FIG. 7 is a heating chamber or oven 70 according to an embodiment of the present invention having valved lines 72 feeding multiple molds or forms 74 with and recirculating a heat transfer fluid to the forms 72 in parallel. The heating chamber doors 71 retain heat.

Figure 8C:
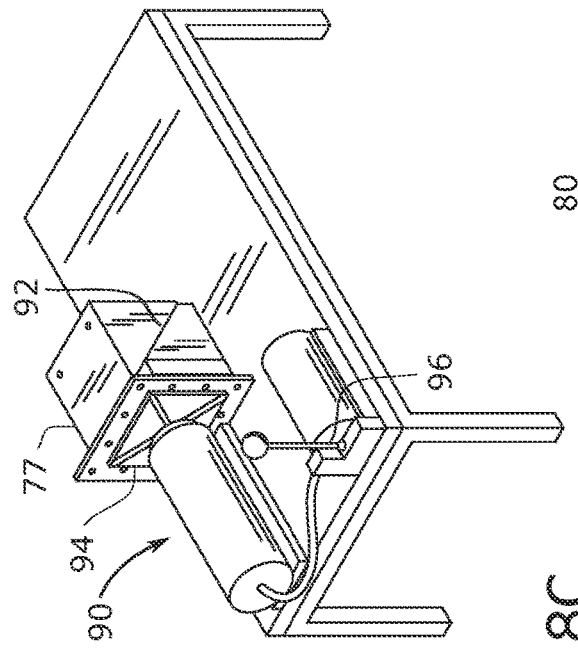
FIG. 8C is a perspective view of a brick extractor apparatus according to an embodiment of the present invention.
Figure 8D:
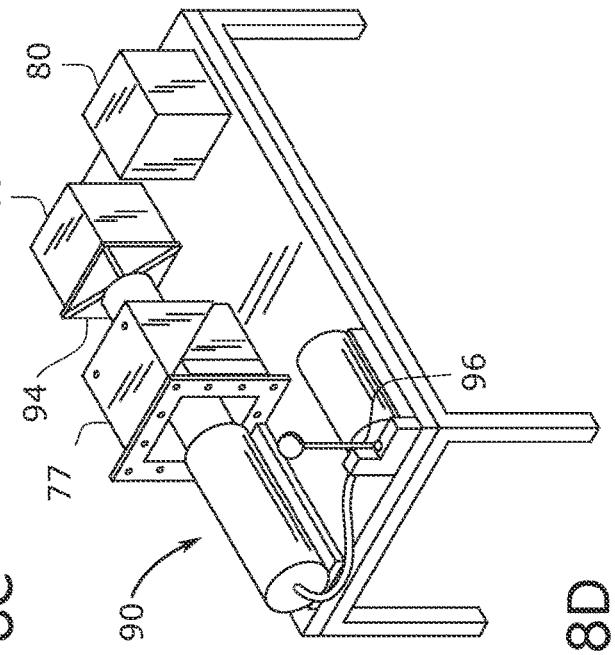
FIG. 8D is a perspective view of the brick extractor apparatus, shown in use.
Figure 8A:
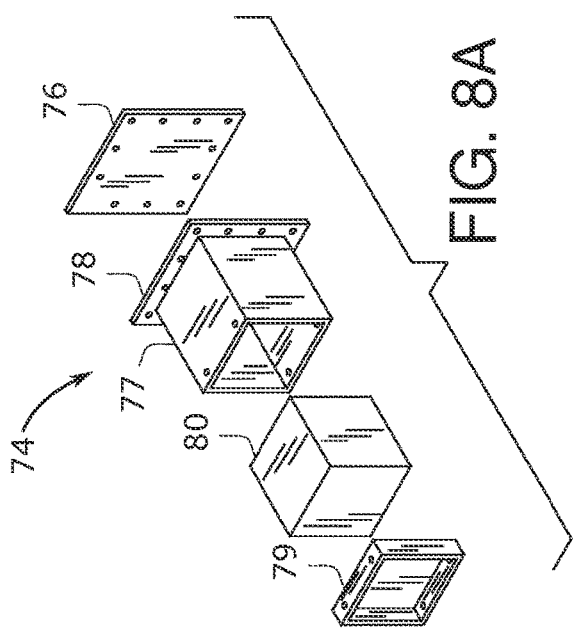
FIG. 8A is an exploded view of a form component of the heating chamber of FIG. 7.
Figure 8B:
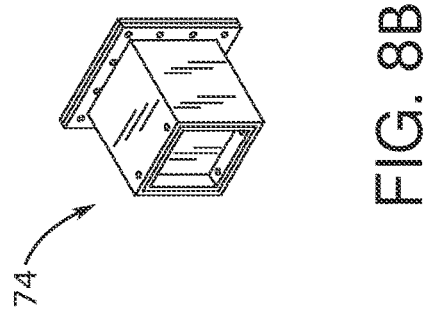
FIG. 8B is a perspective view thereof.

FIGS. 8A and 8B illustrate one of the forms of the heating chamber 70 shown in FIG. 7. The form 74 comprises a form bottom 76, a form body 77 with flanges 78, and a form lid 78 and contains a mycoblock or brick 80. As shown in FIGS. 8C and 8D, the mycoblock 80 may be extracted from the form 74 using a brick extractor apparatus 90 according to an embodiment of the present invention. Once the form bottom 76 has been removed, the form body 77 is placed between brackets 92 with the form lid 78 facing away from the extractor 90. A piston 94, operated with hydraulic lever 96, presses through the form body 77.

Figure 9:
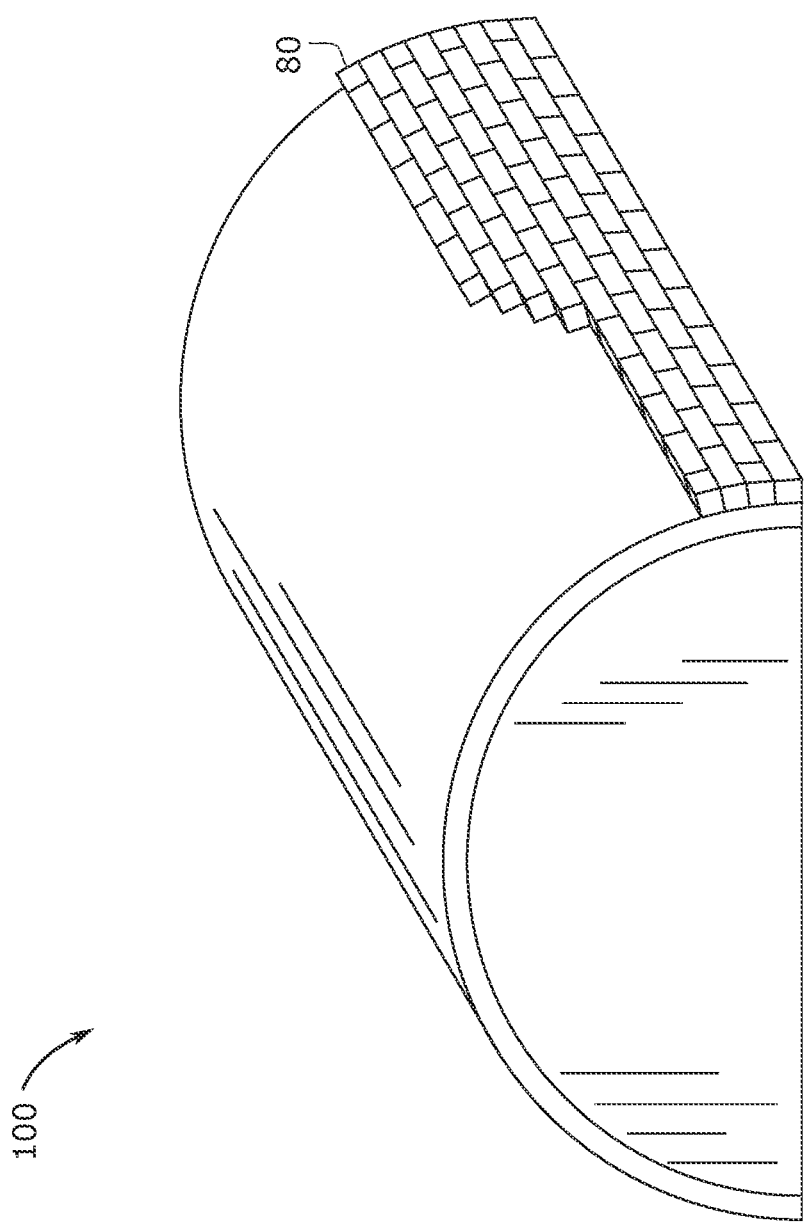
FIG. 9 is a perspective view of an inflatable scaffold according to an embodiment of the present invention, shown in use supporting mycotecture blocks.

As shown in FIG. 9, the mycoblocks 80 may be assembled on an inflatable scaffold 100, enabling relatively cheap, easy, quick and reproducible building construction.

It should be understood, of course, that the foregoing relates to exemplary embodiments of the invention and that modifications may be made without departing from the spirit and scope of the invention as set forth in the following claims.

What is claimed is:

1. A method of making a food source or medicinal composition and of making a mycotecture construction unit, comprising:
(a) cultivating a mycelium/substrate composite and edible mushrooms, including;
(i) forming a mycelium inoculum of a preselected fungus;
(ii) comminuting a substrate;
(iii) soaking the substrate in water;
(iv) draining the water to achieve a substrate moisture content characterized by clumping when squeezed;
(v) pasteurizing the substrate;
(vi) cooling the substrate below about 26° C.;
(vii) after said cooling, inoculating the substrate with the mycelium inoculum;
(viii) growing mycelium in the substrate from the mycelium inoculum; and
(ix) harvesting the edible mushrooms from the mycelium, leaving a mycelium-substrate composite;
(b) and manufacturing the mycotecture construction unit, including;
(i) placing the mycelium-substrate composite into a press having a cavity form with a predetermined shape;
(ii) pressing the mycelium-substrate composite at a predetermined pressure; and
(iii) heating the mycelium-substrate composite while in the form.

2. The method of claim 1, wherein the substrate is a biomass.

3. The method of claim 1, wherein the step of growing the mycelium comprises storing the inoculated substrate in a colonization chamber at about 18° C. and a relative humidity of greater than 10% until the substrate is fully colonized; transferring the fully colonized substrate to a fruiting chamber maintained at about 18° C.; and monitoring for contamination.

4. The method of claim 1, wherein prior to the step of placing the mycelium-substrate composite into the press, the method further comprises collecting, storing, and sealing the mycelium-substrate composite in a temperature-controlled environment; weighing a predetermined amount of the mycelium-substrate composite; and inserting the predetermined amount of the mycelium-substrate composite into a mold.

5. The method of claim 1, wherein the step of placing the mycelium-substrate composite into the press further comprises pressing the mycelium-substrate composite with a tamper out of a growing bag onto a conveyor and conveying the mycelium-substrate composite into the press; and the step of pressing the mycelium-substrate composite further comprises compressing the mycelium-substrate composite for a predetermined period of time, ejecting the mycelium-substrate composite from the press, and transferring the mycelium-substrate composite to a heating chamber.

6. The method of claim 1, wherein the predetermined pressure is about 150 tons.

7. The method of claim 1, wherein the step of heating the mycelium-substrate composite further comprises placing the compressed mycelium-substrate composite in a mold in a heating chamber; heating the heating chamber for about 4 hours; and cooling the mold in a drying room.

8. The method of claim 1, wherein the step of forming a mycelium inoculum comprises manufacturing a mycelium culture comprising:
preparing sterile petri dishes containing sterilized agar; inoculating spores from a mushroom onto the sterilized agar; sealing and labeling the sterile petri dishes; and storing the sterile petri dishes in an inverted position until fully colonized.

9. The method of claim 8, wherein the step of forming the mycelium inoculum further comprises inoculating grain with mycelium from the fully colonized sterile petri dishes.

10. The method of claim 9, wherein prior to inoculating the grain, the method further comprises soaking the grain in water, draining the water from the grain, packing the grain into bottles, sterilizing the bottles containing grain, and cooling the bottles; labeling the bottles; and storing the bottles until fully colonized.

11. The method of claim 9, further comprising adding wheat bran to the grain.

12. The method of claim 1, wherein prior to the step of pasteurizing the substrate, the method further comprises adding lime and wheat bran to the substrate.

13. The method of claim 1, wherein the step of pasteurizing the substrate comprises: packing the substrate into plastic bags; reversibly fastening the plastic bags in a closed configuration; and heating the plastic bags for about 3 hours at about 65° C.

14. The method of claim 1 wherein the step of pasteurizing comprises loading the substrate into a ribbon blender with a predetermined amount of bran; maintaining the substrate and bran at a temperature of about 65° C. while blending for about an hour; and cooling the substrate and bran to below about 26° C.; and wherein the step of inoculating the substrate comprises adding mycelium inoculum in a predetermined amount to the substrate and bran in the ribbon blender and blending for about 10 minutes.

* * * * *